(12) United States Patent
Trefethen et al.

(10) Patent No.: US 11,911,102 B2
(45) Date of Patent: Feb. 27, 2024

(54) OPHTHALMOLOGIC APPARATUS

(71) Applicant: Topcon Corporation, Tokyo (JP)

(72) Inventors: John Thomas Trefethen, Bellingham, WA (US); Thomas Nuzzo, San Francisco, CA (US); Akira Mizuno, Tokyo (JP); Shigeru Okikawa, Tokyo (JP); Yuta Suzuki, Tokyo (JP)

(73) Assignee: Topcon Corporation, Tokyo (JP)

( * ) Notice: Subject to any disclaimer, the term of this patent is extended or adjusted under 35 U.S.C. 154(b) by 208 days.

(21) Appl. No.: 17/069,753

(22) Filed: Oct. 13, 2020

(65) Prior Publication Data
US 2022/0110517 A1     Apr. 14, 2022

(51) Int. Cl.
*A61B 3/00*     (2006.01)
*A61B 3/028*     (2006.01)
*A61B 3/103*     (2006.01)

(52) U.S. Cl.
CPC ............ *A61B 3/0083* (2013.01); *A61B 3/028* (2013.01); *A61B 3/103* (2013.01)

(58) Field of Classification Search
CPC .................................................. A61B 3/0083
USPC ........................................................ 351/245
See application file for complete search history.

(56) References Cited

U.S. PATENT DOCUMENTS

| | | | | |
|---|---|---|---|---|
| 666,856 A * | 1/1901 | Ryer | ......................... | A61B 3/04 351/216 |
| 5,459,536 A * | 10/1995 | Shalon | .................. | A61B 3/0083 351/224 |
| 8,967,808 B2 * | 3/2015 | Antkowiak | ............ | G06V 40/19 351/205 |
| 2004/0032568 A1 | 2/2004 | Fukuma et al. | | |
| 2011/0299038 A1 * | 12/2011 | Antkowiak | .......... | A61B 3/0016 351/221 |

(Continued)

FOREIGN PATENT DOCUMENTS

| CN | 102525401 A | 7/2012 |
|---|---|---|
| CN | 111700754 A * | 9/2020 |

(Continued)

OTHER PUBLICATIONS

Extended European Search Report dated Feb. 15, 2022, in connection with European Patent Application No. 21201287.6, 7 pgs.

*Primary Examiner* — Zachary W Wilkes
(74) *Attorney, Agent, or Firm* — Chiesa Shahinian & Giantomasi PC

(57) ABSTRACT

An ophthalmologic apparatus is provided, which is capable of more securely supporting left and right cheekbone portions of a subject in accordance with the size and shape of the subject's face allowing the subject to respond orally where the positions of the subject's eyes are fixed. The ophthalmologic apparatus includes a forehead contact portion coming into contact with the forehead of the subject, and a cheek contact portion coming into contact with the cheeks of the subject. The cheek contact portion includes a first cheek-contact body that supports one of the cheeks of the subject, a second cheek-contact body that supports the other one of the cheeks of the subject, and an opening/closing mechanism portion that opens and closes in a horizontal direction the first cheek-contact body and the second cheek-contact body in a direction of coming close to each other and a direction of separating from each other.

10 Claims, 12 Drawing Sheets

(56) References Cited

U.S. PATENT DOCUMENTS

2017/0127970 A1* 5/2017 Doran ................... A61B 3/14
2020/0100666 A1* 4/2020 Takii ..................... A61B 3/12

FOREIGN PATENT DOCUMENTS

| CN | 111700754 A | 9/2020 |
| JP | H07-194547 A | 8/1995 |
| JP | H11-313798 A | 11/1999 |
| JP | 2016-214485 A | 12/2016 |

* cited by examiner

OPHTHALMOLOGIC APPARATUS

BACKGROUND OF THE INVENTION

1. Field of the Invention

The present invention relates to an ophthalmologic apparatus.

2. Description of the Related Art

When an examiner such as a doctor examines the eyes of a subject by using an ophthalmologic apparatus, the examiner needs to determine the position of the head or face of the subject to fix the positions of the eyes of the subject with respect to the ophthalmologic apparatus. Japanese Patent Application Publication No. 2016-214485 and Japanese Patent Application Publication No. H07-194547, for example, each disclose a technique for fixing the head of a subject.

A head fixing device for an ophthalmologic apparatus disclosed in Japanese Patent Application Publication No. 2016-214485 includes a forehead support portion coming into contact with the forehead of a subject to support the same, and cheekbone support portions for supporting the weight of the head of the subject by cheekbone portions. The forehead support portion and the cheekbone support portions are connected and fixed to left and right columns. Hence, the positions of the cheekbone support portions are fixed at the respective columns.

The ophthalmologic apparatus disclosed in Japanese Patent Application Publication No. H07-194547 includes a forehead pad provided above an opening of a casing, and abutting members provided below the opening of the casing. The forehead pad is pressed by the forehead of a subject and moves in a direction of an optical path of the ophthalmologic apparatus in accordance with the unevenness of the face of the subject. The abutting members are pressed by regions near the cheekbones and move in the direction of the optical path of the ophthalmologic apparatus in accordance with the unevenness of the face of the subject. The forehead pad and the abutting members push back the face of the subject, move in accordance with the unevenness of the face of the subject, and fix the face of the subject by keeping the balance between action and reaction.

Incidentally, in the head fixing device for an ophthalmologic apparatus disclosed in Japanese Patent Application Publication No. 2016-214485, the forehead of the subject is supported by the forehead support portion, and the cheekbone portions of the subject are supported by the cheekbone support portions. Moreover, in the ophthalmologic apparatus disposed in Japanese Patent Application Publication No. H07-194547, the forehead of the subject is supported by the forehead pad, and the regions near the cheekbones of the subject are supported by the abutting members. More specifically, the ophthalmologic apparatuses disclosed in Japanese Patent Application Publication No. 2016-214485 and Japanese Patent Application Publication No. H07-194547 each do not include a chin rest. For this reason, the chin of the subject is not supported. Therefore, when the subject needs to orally respond to questions and the like of the examiner during, for example, a subjective examination, the subject can orally respond in a state where the positions of the eyes of the subject are fixed to the ophthalmologic apparatus.

However, as descried above, the cheekbone support portions disclosed in Japanese Patent Application Publication No. 2016-214485 are fixed to the columns. Also, the positions of and the distance between the left and right cheekbone portions of the subject vary from subject to subject. Therefore, a problem with the ophthalmologic apparatus disclosed in Japanese Patent Application Publication No. 2016-214485 is that it is difficult to more securely support the left and right cheekbone portions of the subject in accordance with the size and shape of the face of the subject and to allow the subject to be able to orally respond in a state where the positions of the eyes of the subject are fixed.

In the ophthalmologic apparatus disclosed in Japanese Patent Application Publication No. H07-194547, although the abutting members move in the direction of the optical path of the ophthalmologic apparatus in accordance with the unevenness of the face of the subject, the abutting members cannot move in the horizontal direction (i.e., lateral direction) and the up-down direction with respect to the face of the subject. Therefore, a problem with the ophthalmologic apparatus disclosed in Japanese Patent Application Publication No. H07-194547 is that it is difficult to more securely support the left and right cheekbone portions of the subject in accordance with the size and shape of the face of the subject and to allow the subject to be able to orally respond in a state where the positions of the eyes of the subject are fixed.

SUMMARY OF THE INVENTION

The present invention has been contrived to solve the foregoing problems, and an object thereof is to provide an ophthalmologic apparatus capable of more securely supporting the left and right cheekbone portions of a subject in accordance with the size and shape of the face of the subject so that the subject can respond orally while having the positions of the eyes of the subject fixed.

The foregoing problems can be solved by an ophthalmologic apparatus for examining an eye of a subject, the apparatus including: a forehead contact portion coming into contact with a forehead of the subject; and a cheek contact portion coming into contact with cheeks of the subject, wherein the cheek contact portion has a first cheek-contact body that supports one of the cheeks of the subject, a second cheek-contact body that supports the other one of the cheeks of the subject, and an opening/closing mechanism portion that opens and closes in a horizontal direction the first cheek-contact body and the second cheek-contact body in a direction of coming close to each other and a direction of separating from each other.

According to the ophthalmologic apparatus of the present invention, the head or the face of the subject is supported in a three-point support form by the forehead contact portion which is a first support section, the first cheek-contact body which is a second support section, and the second cheek-contact body which is a third support section. The first cheek-contact body and the second cheek-contact body can be opened and closed by the opening/closing mechanism portion in the direction of coming close to each other and the direction of separating from each other in the horizontal direction in accordance with the size and specific shape of the face of the subject. Therefore, the positions of the eyes of the subject are fixed so as not to move with respect to the ophthalmologic apparatus. Moreover, the head or the face of the subject is stably supported comfortably without restraining the chin. The ophthalmologic apparatus according to the present invention, therefore, can more securely support the left and right cheekbone portions of the subject in accordance with the size and shape of the face of the subject in such a manner that the subject can orally respond in a state where the positions of the eyes of the subject are fixed.

In the ophthalmologic apparatus according to the present invention, it is preferred that the first cheek-contact body have at a tip thereof a first contact member, the first contact member having a spherical shape and coming into contact with the one of the cheeks, and that the second cheek-contact body have at a tip thereof a second contact member, the second contact member having a spherical shape and coming into contact with the other one of the cheeks.

According to the ophthalmologic apparatus of the present invention, the first contact member of the first cheek-contact body and the second contact member of the second cheek-contact body are each in a spherical shape, and therefore can support the left and right cheekbone portions of the subject more securely in accordance with the positions and shapes of the cheekbone portions of the subject. Furthermore, since the first contact member and the second contact member are each in a spherical shape, even when the first contact member comes into direct contact with the one of the cheeks of the subject and the second contact member comes into direct contact with the other one of the cheeks of the subject, the head or face of the subject can be supported without discomfort.

In the ophthalmologic apparatus according to the present invention, it is preferred that the opening/closing mechanism portion can open and close the first cheek-contact body and the second cheek-contact body at an angle equal on left and right sides in the horizontal direction with respect to a centerline in a vertical direction.

According to the ophthalmologic apparatus of the present invention, the first cheek-contact body and the second cheek-contact body can be opened and closed by the opening/closing mechanism portion at an angle equal on left and right sides in the horizontal direction. Therefore, the first cheek-contact body and the second cheek-contact body can support the respective cheeks more stably in accordance with the size and specific shape of the face of the subject.

In the ophthalmologic apparatus according to the present invention, it is preferred that the opening/closing mechanism portion can move the first cheek-contact body and the second cheek-contact body so that the first cheek-contact body and the second cheek-contact body are at a same height position with respect to each other in the vertical direction.

According to the ophthalmologic apparatus of the present invention, the opening/closing mechanism portion can move the first cheek-contact body and the second cheek-contact body so that the first cheek-contact body and the second cheek-contact body are at the same height position with respect to each other in the vertical direction of the ophthalmologic apparatus. Therefore, the first cheek-contact body and the second cheek-contact body can be positioned on the respective cheeks while moving in the vertical direction in accordance with the size and specific shape of the face of the subject, thereby supporting the respective cheeks more stably.

In the ophthalmologic apparatus according to the present invention, it is preferred that the opening/closing mechanism portion can move the first cheek-contact body and the second cheek-contact body by rotating the first cheek-contact body and the second cheek-contact body in the vertical direction about an axis extending in the horizontal direction as a center, so that the first cheek-contact body and the second cheek-contact body are at a same height position with respect to each other.

According to the ophthalmologic apparatus of the present invention, the opening/closing mechanism portion can move the first cheek-contact body and the second cheek-contact body by rotating the first cheek-contact body and the second cheek-contact body in the vertical direction of the ophthalmologic apparatus about the axis extending in the horizontal direction as a center so that the first cheek-contact body and the second cheek-contact body are at the same height position with respect to each other. Thus, the first cheek-contact body and the second cheek-contact body can be positioned on the respective cheeks while rotating in the vertical direction in accordance with the size and specific shape of the face of the subject, thereby supporting the respective cheeks more stably.

In the ophthalmologic apparatus according to the present invention, it is preferred that the ophthalmologic apparatus be a subjective examination apparatus.

In conducting a subjective examination on the eyes of the subject, the ophthalmologic apparatus according to the present invention can prevent the chin and the mouth of the subject from being restrained, while stably and securely determining the positions of the eyes with respect to the ophthalmologic apparatus in accordance with the size and specific shape of the face of the subject. Therefore, in order to carry out a subjective examination on the eyes of the subject, the ophthalmologic apparatus of the present invention can support the left and right cheekbone portions of the subject more securely in accordance with the size and shape of the face of the subject, so that the subject can respond orally in a state where the positions of the eyes of the subject are fixed.

In the ophthalmologic apparatus according to the present invention, it is preferred that the subjective examination apparatus be attached to a pedestal in a state of being suspended.

According to the ophthalmologic apparatus of the present invention, even in a state in which the subjective examination apparatus is suspended on the pedestal, in order to perform a subjective examination on the eyes of the subject, the chin and the mouth of the subject can be prevented from being restrained, while having the positions of the eyes determined stably and securely with respect to the ophthalmologic apparatus in accordance with the size and specific shape of the face of the subject. Thus, in order to perform a subjective examination on the eyes of the subject using the suspended subjective examination apparatus, the ophthalmologic apparatus according to the present invention can support the left and right cheekbone portions of the subject more securely in accordance with the size and shape of the face of the subject in such a manner that the subject can respond orally in a state where the positions of the eyes of the subject are fixed.

In the ophthalmologic apparatus according to the present invention, it is preferred that the subjective examination apparatus be an objective/subjective examination apparatus for performing subjective refraction optometry and objective refraction optometry.

In conducting subjective refraction optometry and objective refraction optometry, the ophthalmologic apparatus according to the present invention can determine the positions of the eyes of the subject with respect to the ophthalmologic apparatus stably and securely in accordance with the size and specific shape of the face of the subject. Since the chin and the mouth of the subject are not restrained, the subject can respond orally. Consequently, objective refraction optometry and subjective refraction optometry can be executed smoothly.

In the ophthalmologic apparatus according to the present invention, it is preferred that the cheek contact portion be attached to a base portion by a support member in a detachable manner, and that a schematic eye holder for mounting a schematic eye for calibration can be attached to the base portion in place of the support member.

According to the ophthalmologic apparatus of the present invention, the cheek contact portion is attached to the base portion by the support member in a detachable manner. Also, the schematic eye holder for mounting the schematic eye can be attached to the base portion in place of the support member supporting the cheek contact portion. Therefore, optical calibration (correction) of the ophthalmologic apparatus according to the present invention can reliably executed.

The present invention can provide an ophthalmologic apparatus capable of more securely supporting the left and right cheekbone portions of a subject in accordance with the shape of the face of the subject so that the subject can respond orally in a state where the positions of the eyes of the subject are fixed.

DESCRIPTION OF THE PREFERRED EMBODIMENTS

Figure 1:
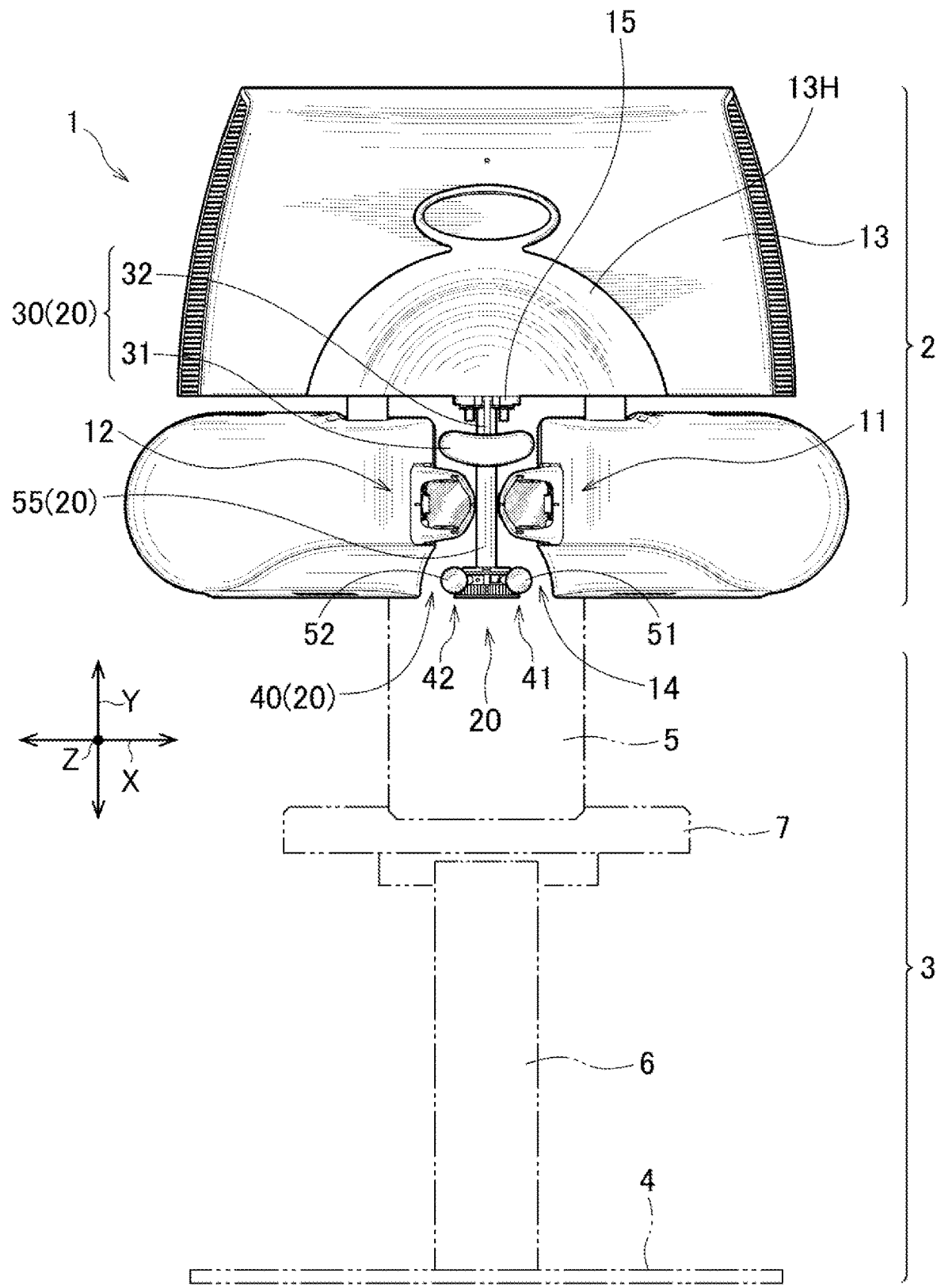
FIG. 1 is a front view showing a binocular objective/subjective examination apparatus which is an example of an ophthalmologic apparatus according to an embodiment of the present invention.

Preferred embodiments of the present invention are now described hereinafter in detail with reference to the drawings.

Note that, since the embodiments described below are favorable specific examples of the present invention, various technically favorable limits are applied thereto; however, the scope of the present invention is not limited to these embodiments unless the following description specifically states that the present invention is limited. Further, in each drawing, identical components are designated the same reference numerals; thus, detailed descriptions thereof are omitted accordingly.

First Embodiment

Overview of an Example of an Ophthalmologic Apparatus according to an Embodiment of the Present Invention FIG. 1 is a front view showing a binocular objective/subjective examination apparatus which is an example of an ophthalmologic apparatus according to an embodiment of the present invention.

Figure 2:
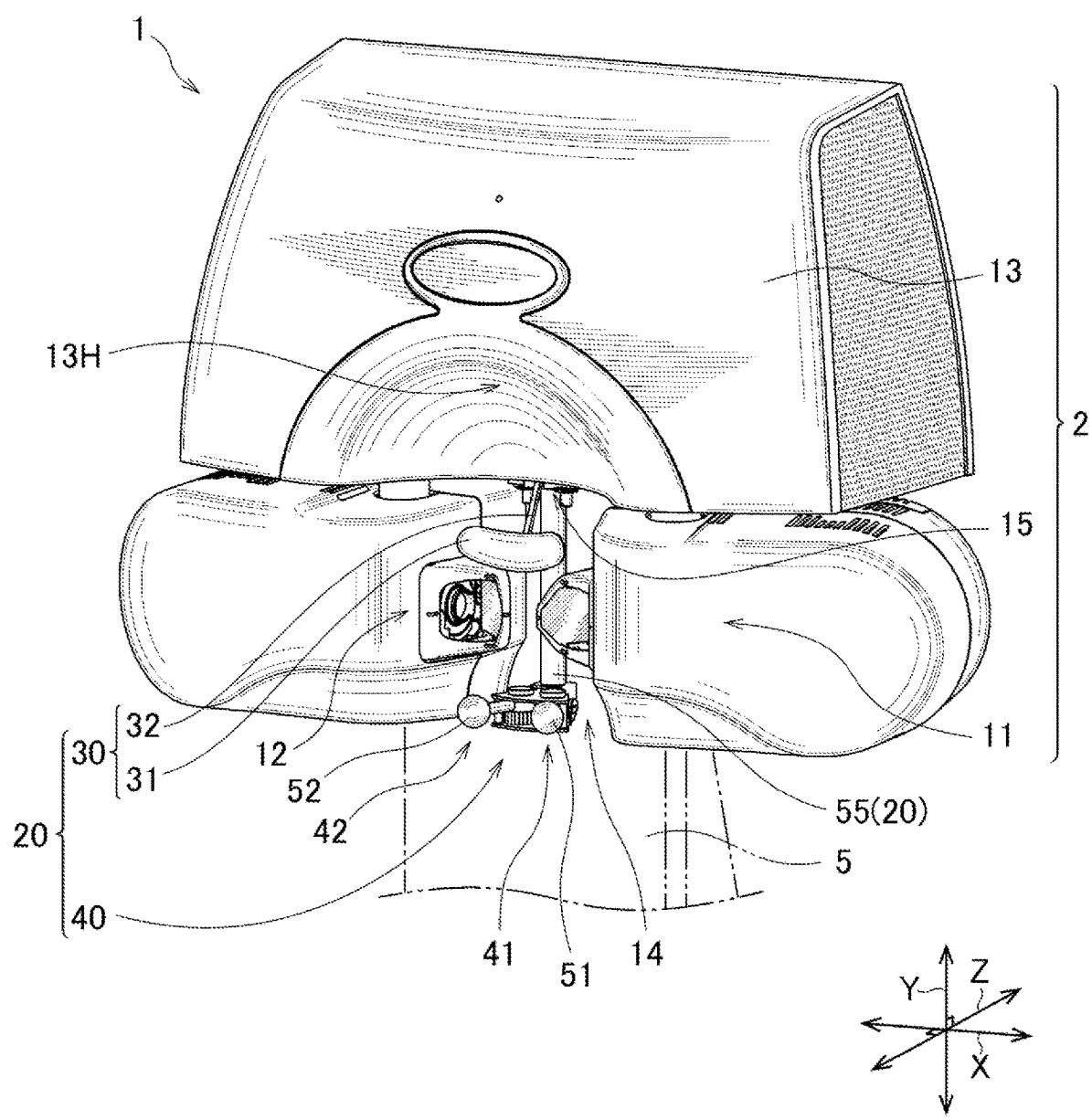
FIG. 2 is a perspective view showing the binocular objective/subjective examination apparatus shown in FIG. 1.

FIG. 2 is a perspective view showing the binocular objective/subjective examination apparatus shown in FIG. 1.

Note that FIG. 2 omits the illustration of a part of a pedestal.

A binocular objective/subjective examination apparatus 1 shown in FIGS. 1 and 2 include an examination apparatus main body 2 and a pedestal 3. The binocular objective/subjective examination apparatus 1 according to the present embodiment is an example of the "ophthalmologic apparatus" of the present invention. The examination apparatus main body 2 is supported on the pedestal 3. The pedestal 3 has a flat plate-like base portion 4 placed on the floor, column portions 5, 6, and a table 7. The examination apparatus main body 2 is provided in a suspended manner at an upper end portion of the column portion 5. It is preferred that the examination apparatus main body 2 be fixed so as to be detachable with respect to the column portion 5. In the present specification, a lateral direction of the binocular objective/subjective examination apparatus 1 is indicated as an X direction, an up-down direction of the binocular objective/subjective examination apparatus 1 (i.e., vertical direction) is indicated as a Y direction, and a front-back direction (depth direction) of the binocular objective/subjective examination apparatus 1 is indicated as a Z direction.

As shown in FIGS. 1 and 2, the examination apparatus main body 2 of the binocular objective/subjective examination apparatus 1 has a first eyepiece portion 11, a second eyepiece portion 12, a main body base portion 13, and a head fixing device 20. The first eyepiece portion 11 is provided to the right of the head fixing device 20 as viewed from a subject (as viewed from the direction perpendicular to the page of FIG. 1), to show a visual target and the like to the left eye of the subject and acquire information on the characteristics of the right eye of the subject. The second eyepiece portion 12 is provided to the left of the head fixing device 20 as viewed from the subject (as viewed from the direction perpendicular to the page of FIG. 1), to show a visual target and the like to the left eye of the subject and acquire information on the characteristics of the right eye of the subject. The first eyepiece portion 11, the second eyepiece portion 12, and the main body base portion 13 are each provided with an examination optical system. The binocular objective/subjective examination apparatus 1 has a simultaneous objective refraction measurement function for both eyes of the subject, and a simultaneous subjective refraction measurement function for both eyes of the subject. The first eyepiece portion 11 and the second eyepiece portion 12 are provided below the main body base portion 13. A space portion 14 is provided between the first eyepiece portion 11 and the second eyepiece portion 12. The main body base portion 13 is provided with a depressed curved portion 13H in order to avoid a part of the head of the subject that is above the forehead of the subject.

The objective refraction examination described herein means an examination that ignores senses of the subject.

According to the objective refraction examination, examination items such as myopia and hyperopia can be tested even on infants and unconscious subjects. The subjective refraction examination means an examination that focuses on senses of the subject. Since the subjective refraction examination requires the subject to respond orally, it is difficult to test the examination items such as myopia and hyperopia on infants and unconscious subjects. In the binocular objective/subjective examination apparatus 1, the objective refraction examination is performed on both eyes of the subject simultaneously, and upon completion of the objective refraction examination, the interactive subjective refraction examination between an examiner such as a doctor and an oral response of the subject is performed based on the objective refraction examination.

Note that examples of a case where the subject is required to respond during an eye exam, that is, a case where the subject has no choice but responding orally, include examinations requiring subjective responses (subjective refraction examination, visual performance examination, visual field examination), responses about fixation targets (fixation targets include the center, periphery, symbols, visual targets, diagrams, images, videos, etc.), responses to questions from the examiner, responses to checking on the health of the subject (e.g., "are you sleepy?" "your eyes are closing", "are you feeling okay?") (examples of the responses to these questions include "I am tired", "I need a short break", etc.).

Head Fixing Device 20

A structure of the head fixing device 20 is described next.

Figure 3:
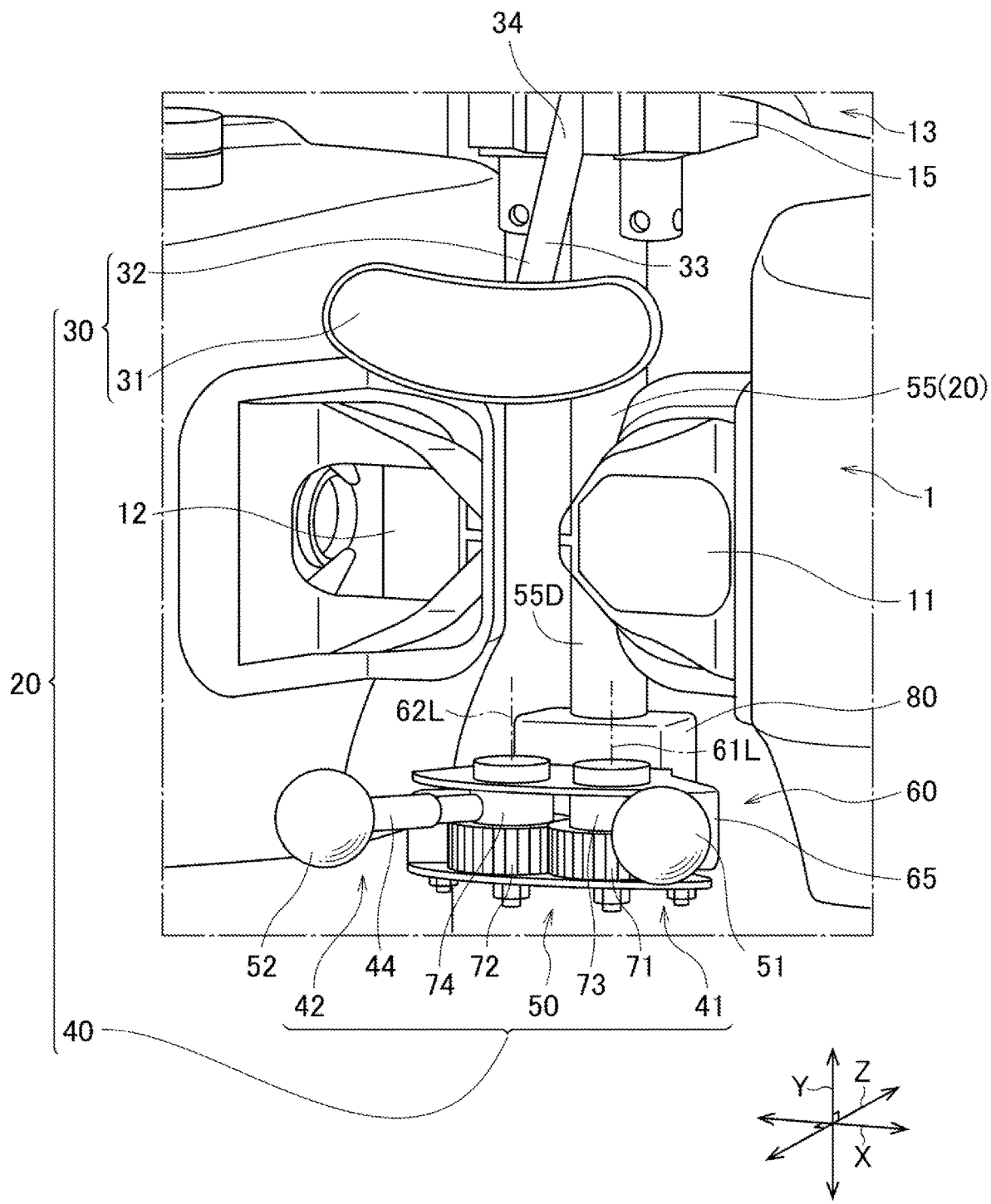
FIG. 3 is a perspective view showing an enlargement of a head fixing device of the present embodiment.

FIG. 3 is a perspective view showing an enlargement of the head fixing device of the present embodiment.

Figure 4:
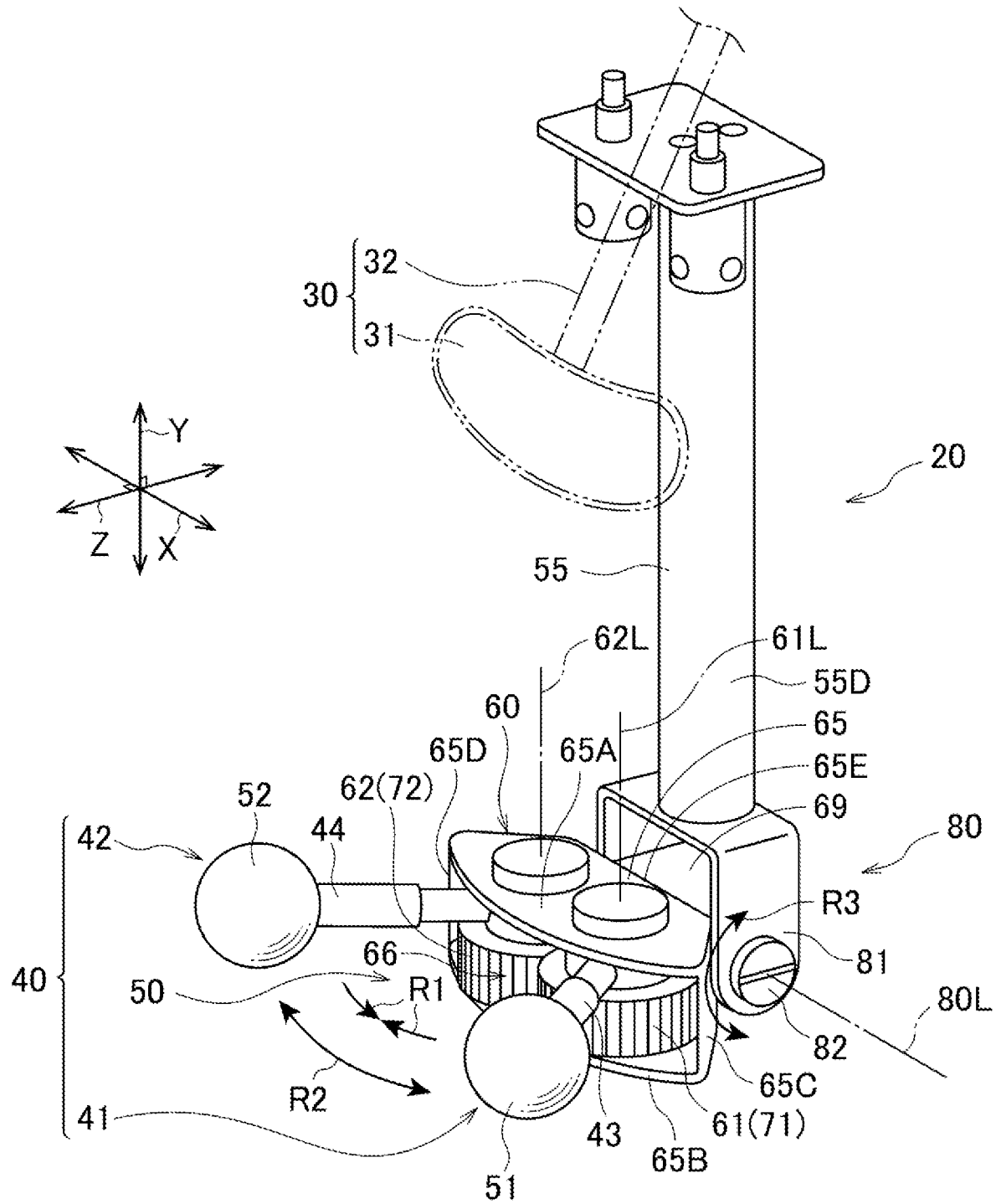
FIG. 4 is a perspective view showing the head fixing device of the present embodiment.

FIG. 4 is a perspective view showing the head fixing device of the present embodiment.

As shown in FIGS. 1 and 2, the head fixing device 20 is provided in the space portion 14 of the binocular objective/subjective examination apparatus 1. Specifically, as shown in FIGS. 1 and 2, the head fixing device 20 is disposed in such a manner as to be suspended along the Y direction at the space portion 14 of the main body base portion 13 of the binocular objective/subjective examination apparatus 1. As shown in FIGS. 1 and 3, the head fixing device 20 is made of metal or plastic, and has a forehead contact portion 30, a cheek contact portion 40, and a rod-shaped support member 55.

Forehead Contact Portion 30

First, the forehead contact portion 30 of the head fixing device 20 is described with reference to FIGS. 1 and 3. The forehead contact portion 30 is a part that comes into contact with the forehead of the subject to support the forehead, and has a forehead rest surface 31 and a rod-shaped supporting member 32. The forehead rest surface 31 is shaped so as to match the curved shape of the forehead of the subject, and has, for example, a depressed curved surface so as to be able to support the forehead of the subject. As shown in FIG. 3, one end portion 33 of the supporting member 32 is connected to the back of the forehead rest surface 31. Preferably, the forehead rest surface 31 is attached in such a manner that the angle thereof with respect to the one end portion 33 of the supporting member 32 can be changed. In this manner, the forehead rest surface 31 can come into contact with the forehead of the subject in accordance with the size and shape of the specific face of the subject, to stably support the forehead of the subject.

As shown in FIG. 3, the supporting member 32 is fixed to a base connecting portion 15 of the main body base portion 13 in such a manner as to extend downward from the base connecting portion 15 to the front side. Another end portion 34 of the supporting member 32 is fixed to the base connecting portion 15 by means of, for example, screws or the like. Preferably, the supporting member 32 is fixed in a detachable manner to the base connecting portion 15. Therefore, the forehead contact portion 30 is removable separately from the support member 55 at the time of maintenance or the like of the binocular objective/subjective examination apparatus 1.

A member made of a biocompatible material that is soft to the touch when the subject brings his/her forehead into contact with the forehead rest surface 31, such as rubber film, silicon film, or non-woven fabric, may be stuck in a detachable manner to the forehead rest surface 31. Since the examiner can pay attention to hygiene by replacing the member stuck to the forehead rest surface 31 each time the subject changes, the subject can place his/her forehead on the forehead rest surface 31 to support his/her forehead without discomfort.

Cheek Contact Portion 40

The cheek contact portion 40 of the head fixing device 20 is described next with reference to FIGS. 3 and 4.

The cheek contact portion 40 is a part that comes into contact with the left and right cheekbone portions of the subject simultaneously, to support the left and right cheekbone portions. The cheek contact portion 40 includes a first cheek-contact body 41, a second cheek-contact body 42, and an opening/closing mechanism portion 50 of the cheek contact portion. The first cheek-contact body 41 supports the right cheek of the subject, which is one of the cheeks, by coming into contact therewith. The second cheek-contact body 42 supports the left cheek of the subject, which is the other cheek, by coming into contact therewith.

As shown in FIG. 4, the first cheek-contact body 41 has a shaft portion 43 and a first contact member 51 having a spherical shape. The first contact member 51 having a spherical shape is fixed to a tip of the shaft portion 43. Similarly, the second cheek-contact body 42 has a shaft portion 44 and a second contact member 52 having a spherical shape. The second contact member 52 having a spherical shape is fixed to a tip of the shaft portion 44. In a case where the first contact member 51 and the second contact member 52 are fixed in a detachable manner to the respective shaft portions 43, 44, the examiner, from a hygienic perspective, can replace the first contact member 51 and the second contact member 52 as necessary, each time when the subject changes. For example, female screws are formed on the first contact member 51 and the second contact member 52. On the other hand, male screws are formed on the tips of the shaft portions 43, 44. For this reason, the first contact member 51 and the second contact member 52 are fixed in a detachable manner to the shaft portions 43, 44. Note that the first cheek-contact body 41 and the second cheek-contact body 42 may have an identical structure. Furthermore, the shaft portion 43 and the first contact member 51 having a spherical shape may be formed integrally. The shaft portion 44 and the second contact member 52 having a spherical shape, too, may be formed integrally.

Since the first contact member 51 and the second contact member 52 are spherical objects, the right and left cheekbone portions of the subject can be supported more securely in accordance with the positions and shapes of the cheekbone portions of the subject. Again, since the first contact member 51 and the second contact member 52 are spherical objects, the head or face of the subject can be supported without discomfort even when the first contact member 51 comes into direct contact with the position of the right cheekbone of the subject and the second contact member 52 comes into direct contact with the left cheekbone of the subject. Examples of materials for the first contact member 51 and the second contact member 52 that come into direct contact with the face of the subject include a relatively soft material that has little physical impact on the subject and is biocompatible, such as an elastic material using rubber such as silicon.

Next, the opening/closing mechanism portion 50 of the cheek contact portion of the head fixing device 20 is described with reference to FIGS. 4 and 5.

Figure 5:
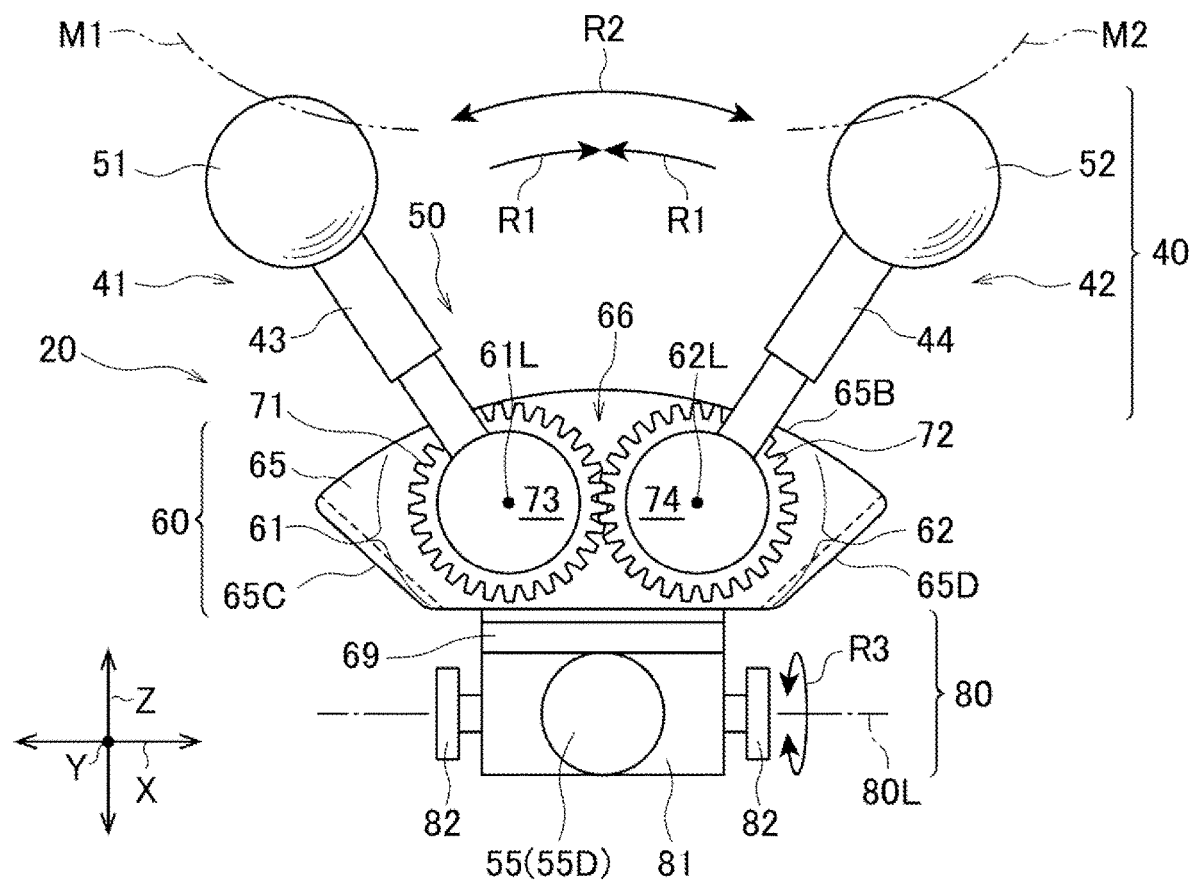
FIG. 5 is a plan view in which the head fixing device of the present embodiment is viewed from above.

FIG. 5 is a plan view in which the head fixing device of the present embodiment is viewed from above.

The opening/closing mechanical portion 50 of the cheek contact portion 40 supports the first cheek-contact body 41 and the second cheek-contact body 42 in such a manner that the first cheek-contact body 41 and the second cheek-contact body 42 can open and close evenly to the left and right in synchronization in directions R1 of coming close to each other and in a direction R2 of separating from each other. The directions R1 and R2 are opposite to each other. Further, the opening/closing mechanism portion 50 of the cheek contact portion 40 rotate the first cheek-contact body 41 and the second cheek-contact body 42 to the same positions in the up-down direction (within Y-Z plane) along a rotation direction R3 shown in FIG. 4.

The opening/closing mechanical portion 50 of the cheek contact portion 40 has a horizontal even opening/closing mechanism 60 for opening and closing the first cheek-contact body 41 and the second cheek-contact body 42 evenly to the left and right in, for example, the horizontal direction (within X-Z plane). The horizontal even opening/closing mechanism 60 is capable of opening/closing the first cheek-contact body 41 and the second cheek-contact body 42 at an angle equal on left and right sides in, for example, the horizontal direction, with respect to the axis in the Y direction as the center, the axis being the centerline in the vertical direction.

Preferred structural examples of the horizontal even opening/closing mechanism 60 are now described with reference to FIGS. 4 and 5.

The horizontal even opening/closing mechanism 60 has a base portion 65, a first rotating body 61, and a second rotating body 62. The base portion 65 is formed of substantially fan-shaped upper plate 65A and lower plate 65B, side plates 65C and 65D, and a back plate 65E, and has a front opening portion 66. The base portion 65 supports the first rotating body 61 and the second rotating body 62 in a rotatable manner, and accommodates therein the first rotating body 61 and the second rotating body 62 side by side.

As shown in FIG. 5, the first rotating body 61 and the second rotating body 62 share the same structure. In the base portion 65, the first rotating body 61 is supported so as to be rotatable about a rotational central axis 61L. Similarly, in the base portion 65, the second rotating body 62 is supported so as to be rotatable about a rotational central axis 62L. As shown in FIG. 5, the first rotating body 61 has a gear 71 and a circular attachment portion 73. The second rotating body 62 has a gear 72 and a circular attachment portion 74.

As shown in FIG. 5, the gears 71 and 72 have the same number of teeth of the same size. The gears 71 and 72 mesh with each other. The circular attachment portion 73 is fixed above the gear 71, and has the shaft portion 43 fixed along a diametrical direction. Similarly, the circular attachment portion 74 is fixed above the gear 72, and has the shaft portion 44 fixed along the diametrical direction. Therefore, when the first contact member 51 and the second contact member 52 come into contact with a right cheek M1 (see FIGS. 6 and 7) and a left cheek M2 (see FIGS. 6 and 7) of the subject respectively, the first contact member 51 and the second contact member 52 can be opened and closed evenly to the left and right in the directions R1 of coming close to each other and in the direction R2 of separating from each other in accordance with the positions of the right cheek M1 and the left cheek M2. Opening the first contact member 51 of the first cheek-contact body 41 and the second contact member 52 of the second cheek-contact body 42 evenly to the left and right can prevent the face and head of the subject from being supported in a tilted manner.

As and shown in FIGS. 4 and 5, the opening/closing mechanism portion 50 of the cheek contact portion 40 also has an up-down direction rotation mechanism 80 in addition to the horizontal even opening/closing mechanism 60. The up-down direction rotation mechanism 80 is fixed to a lower end portion 55D of the rod-shaped or cylindrical support member 55 and supports the horizonal even opening/closing mechanism 60 so as to be turnable in the up-down direction (within Y-Z plane) along the rotation direction R3.

As shown in FIG. 5, the up-down direction rotation mechanism 80 has a fixture 81 having a substantially inverted U-shape. The fixture 81 is fixed to the lower end portion 55D of the support member 55. The fixture 81 has an adjusting screw 82. The adjusting screw 82 supports a protrusion 69 of the horizontal even opening/closing mechanism 60 in the fixture 81. For example, when the examiner or the like rotates the adjusting screw 82 using a specialized tool, the entire horizontal even opening/closing mechanism 60 turns in the up-down direction (within Y-Z plane) along the rotation direction R3. As a result, the first contact member 51 of the first cheek-contact body 41 and the second contact member 52 of the second cheek-contact body 42 move up and down evenly in the direction R3, with respect to an up-down turning central axis 80L as the center, the up-down turning central axis 80L extending in the horizontal direction. Subsequently, the first contact member 51 and the second contact member 52 are positioned at the same position in the up-down direction (within Y-Z plane). In a case where the cheek contact portion 40 is not necessary, the examiner or the like can turn the entire horizontal even opening/closing mechanism 60, for example, downward along the rotation direction R3, to pull the cheek contact portion 40 away from the examiner and the subject.

Thus, when the first contact member 51 of the first cheek-contact body 41 and the second contact member 52 of the second cheek-contact body 42 that are integrated with the horizontal even opening/closing mechanism 60 are turned in the direction R3, the height position of the first contact member 51 on the right and the height position of the second contact member 52 on the left with respect to the Y direction are the same. Specifically, when the entire horizontal even opening/closing mechanism 60 is rotated by the up-down direction rotation mechanism 80 in the direction R3 around the up-down turning central axis 80L extending in the horizontal direction, with respect to the up-down direction of the binocular objective/subjective examination apparatus 1 shown in FIG. 1, the first contact member 51 and the second contact member 52 are disposed in the same height position. As a result, the right cheek M1 and the left cheek M2 of the subject are supported by the first contact member 51 and the second contact member 52 having the spherical shape, at the same height position in the up-down direction (Y direction) of the ophthalmologic apparatus. In addition, while preventing the face of the subject from tilting, the right cheek M1 and the left cheek M2 of the subject can be supported stably without discomfort. Since the up-down direction rotation mechanism 80 can move the first cheek-contact body 41 and the second cheek-contact body 42 evenly so that the first cheek-contact body 41 and the second cheek-contact body 42 are disposed at the same height position with respect to the up-down direction (Y direction) of the ophthalmologic apparatus, the first cheek-contact body 41 and the second cheek-contact body 42 can position the right cheek M1 and the left cheek M2 at the same height position while moving in the up-down direction in accordance with the size and specific shape of the face of the subject. Accordingly, the binocular objective/subjective examination apparatus 1 according to the present embodiment can support the right cheek M1 and the left cheek M2 more stably.

Examples of Use of Head Fixing Device 20

Figure 6:
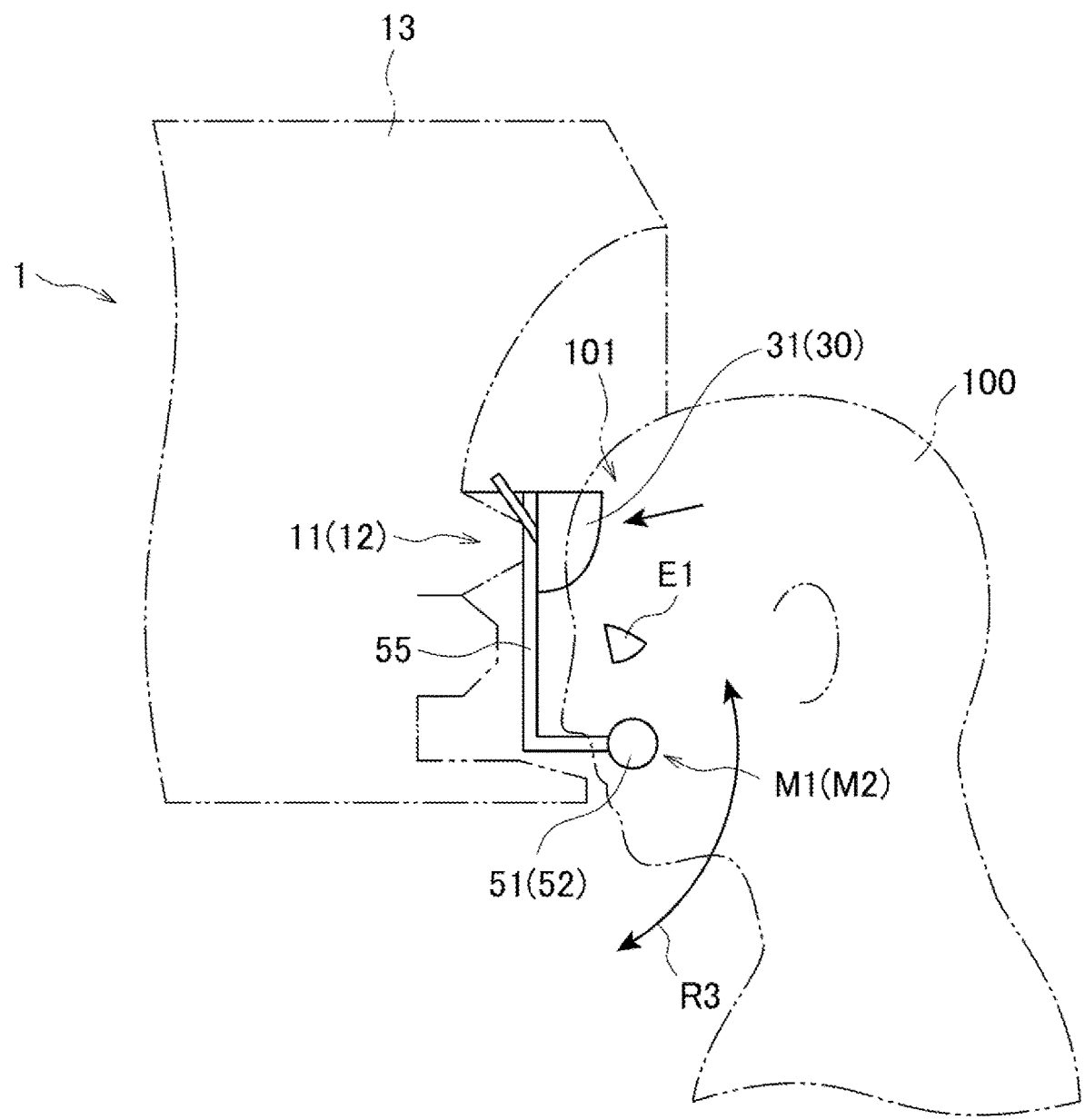
FIG. 6 is a schematic diagram showing an example in which the head fixing device of the present embodiment supports the head or face of a subject.
Figure 7:
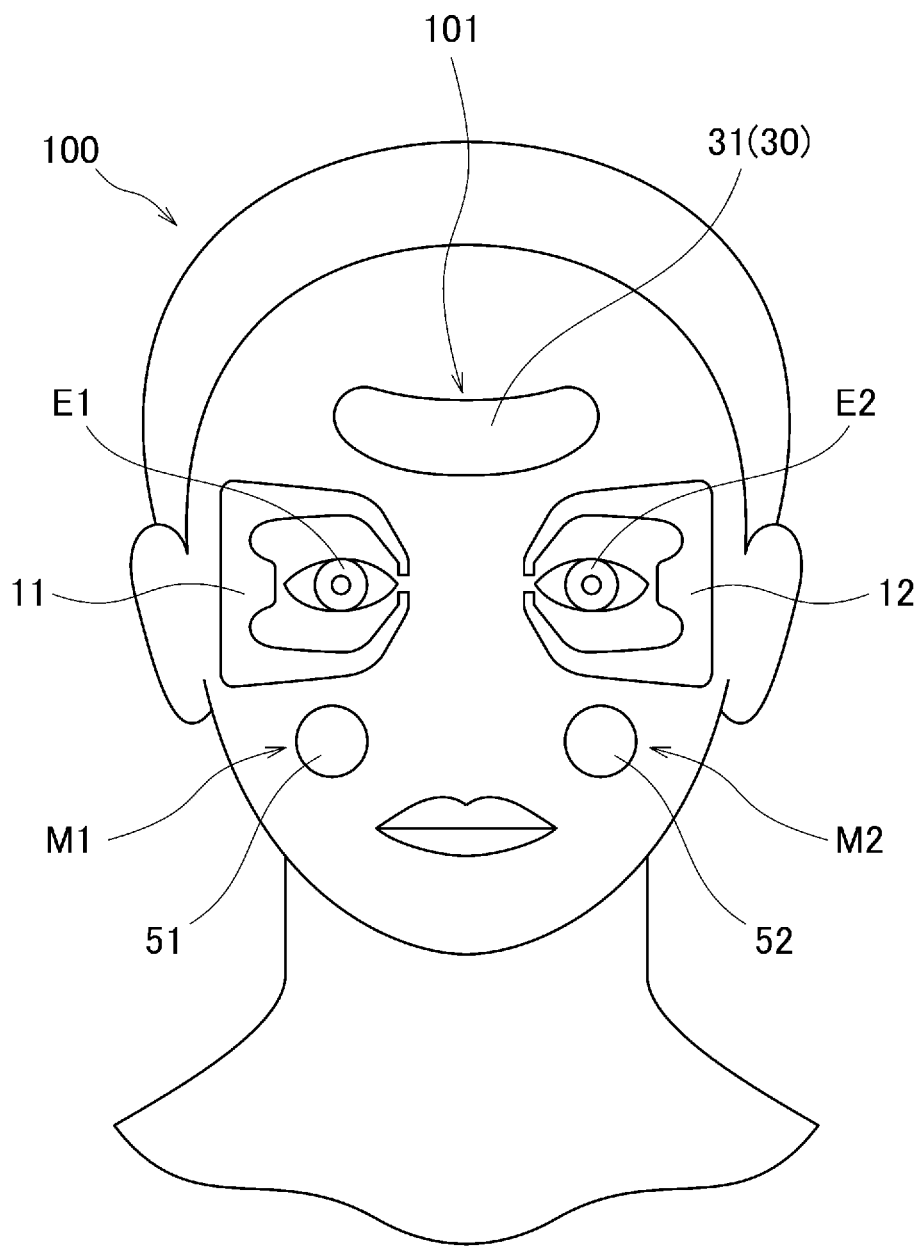
FIG. 7 is a schematic diagram showing a state in which the face, forehead, right cheek, and left cheek of the subject are supported.

Next is described, with reference to FIGS. 6 to 8, an example in which the positions of the eyes of the subject are fixed by supporting the head or face of the subject using the head fixing device 20 so that the head or face of the subject does not move with respect to the binocular objective/subjective examination apparatus 1 shown in FIG. 1, when an objective refraction examination and a subjective refraction examination are executed on both eyes using the binocular objective/subjective examination apparatus 1.

FIG. 6 is a schematic diagram showing an example in which the head fixing device of the present embodiment supports the head or face of the subject.

FIG. 7 is a schematic diagram showing a state in which the face, forehead, right cheek, and left cheek of the subject are supported.

Figure 8A:
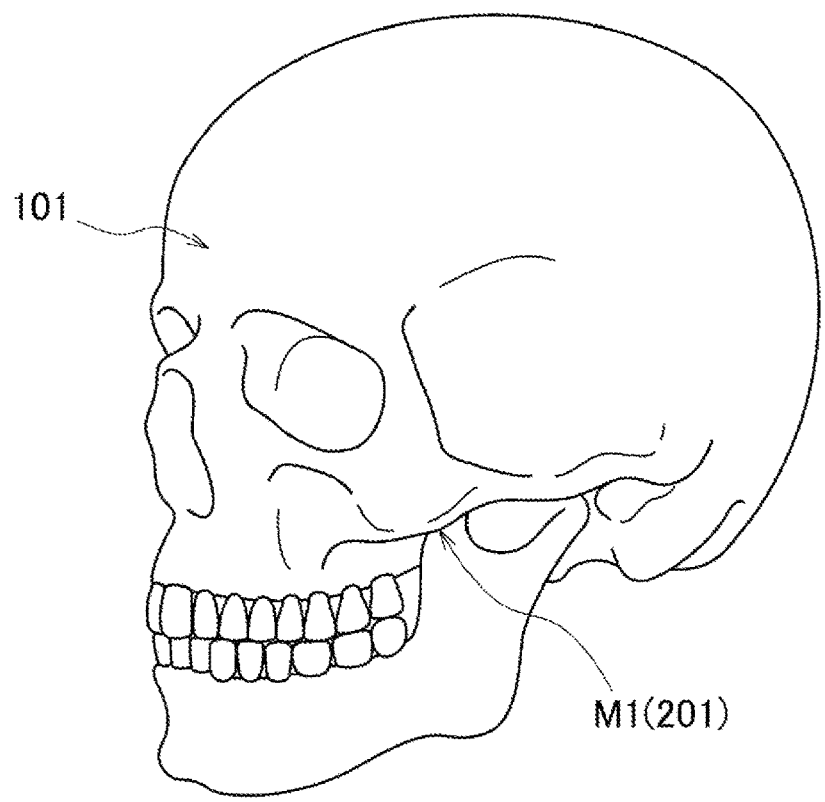
FIGS. 8A and 8B are schematic diagrams showing an example of the skull of the subject.
Figure 8B:
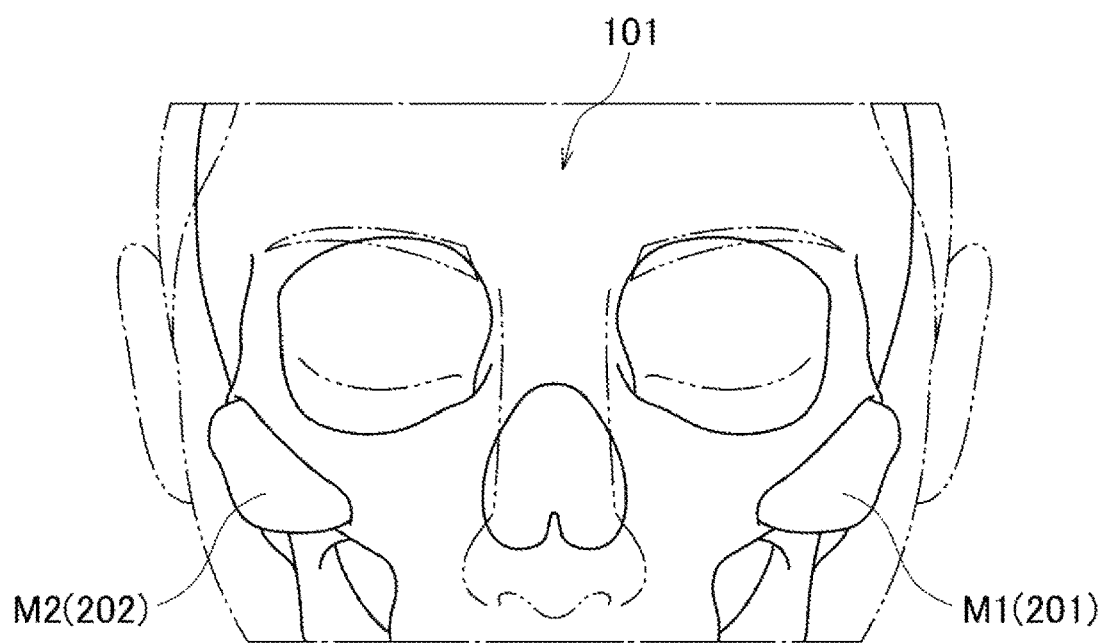

FIGS. 8A and 8B are schematic diagrams showing an example of the skull of the subject.

Note that FIG. 8A is a side view showing the skull of the subject. FIG. 8B is a plan view in which the skull of the subject is viewed from the front.

In FIG. 6, the forehead rest surface 31 of the forehead contact portion 30 supports a forehead 101 of a subject 100 in contact therewith. The forehead rest surface 31 can support the forehead 101 of the subject 100 by following the curved shape of the forehead 101. It is preferred that the forehead rest surface 31 be attached in such a manner that the angle thereof with respect to the one end portion 33 of the supporting member 32 can be changed. The forehead rest surface 31 can stably support the forehead 101 of the subject 100 in contact therewith, in accordance with the size and shape of the specific face of the subject 100. Moreover, since the first contact member 51 and the second contact member 52 are spherical objects, when the first contact member 51 comes into direct contact with the right cheek M1 of the subject 100 and the second contact member 52 comes into direct contact with the left cheek M2 of the subject 100, the head or face of the subject 100 can be supported without discomfort.

In FIG. 7 showing the face of the subject 100, the position where the forehead rest surface 31 comes into contact with the forehead 101, the positions where the first contact member 51 and the second contact member 52 come into contact with the right cheek M1 and the left cheek M2 respectively, and the positions where the first eyepiece portion 11 and the second eyepiece portion 12 approach a right eye E1 and a left eye E2 respectively, are shown. FIG. 7 also shows a state in which the head or face of the subject 100 is supported in a three-point support form by the forehead rest surface 31, the first contact member 51, and the second contact member 52.

In the skull shown in FIGS. 8A and 8B, the forehead rest surface 31 shown in FIG. 6 comes into contact with and supports a bone portion at a position of the forehead 101 of the subject (a part in the frontal bone), and the first contact member 51 and the second contact member 52 shown in FIG. 6 come into contact with and support a part of a cheekbone 201 of the right cheek M1 and a part of a cheekbone 202 of the left cheek M2, respectively. Therefore, the head fixing device 20 can support the head or face of the subject stably at the part of the frontal bone and a part of the sternum without going through a mandible part.

Therefore, the head or face of the subject 100 is stably supported in a three-point support form by the forehead rest surface 31 which is the first support section, the first contact member 51 which is the second support section, and the second contact member 52 which is the third support section. The first cheek-contact body 41 and the second cheek-contact body 42 can be opened and closed by the opening/closing mechanism portion 50 of the cheek contact portion 40 in the direction R1 of coming close to each other and the direction R2 of separating from each other, in accordance with the size and specific shape of the face of the subject. Thus, the positions of the eyes E1, E2 of the subject 100 shown in FIG. 7 are fixed stably so as not to move with respect to the binocular objective/subjective examination apparatus 1 which is the ophthalmologic apparatus. Moreover, the head or face of the subject is supported stably without discomfort, without having the chin restrained. Consequently, the head fixing device 20 can stably and securely determine the positions of the eyes E1, E2 with respect to the binocular objective/subjective examination apparatus 1 by means of the three-point support form, in accordance with the size and specific shape of the face of the subject 100. Furthermore, since the chin and mouth are not restrained, the subject 100 can respond orally during an eye exam, thereby realizing smooth objective refraction optometry and subjective refraction optometry.

In this manner, the head fixing device 20 shown in FIG. 4 can support the skull of the subject stably by the three-point support form in such a manner that the positions of the eyes E1, E2 do not move with respect to the binocular objective/subjective examination apparatus 1. The chin and mouth of the subject are not restrained and therefore are in a free state. For this reason, the subject can freely respond orally to questions and the like from the examiner. As described above, the ophthalmologic apparatus according to the present embodiment can securely support the parts of the right and left cheekbones 201, 202 of the subject in accordance with the size and shape of the face of the subject, so that the subject can orally respond while having the positions of the eyes of the subject fixed. Since the skull is supported by the three-point support form, the positions of the eyes of the subject can be kept easily when an examination is performed with the binocular objective/subjective examination apparatus 1.

The first contact member 51 and the second contact member 52 on the right and left are supported at the same height position with respect to the Y direction which is the up-down direction of the binocular objective/subjective examination apparatus 1, and can be opened at an angle equal on the left and right sides in, for example, the horizontal direction, with respect to the Y direction as the center. The first contact member 51 and the second contact member 52 can therefore support, more stably, the face of the subject so as not to tilt the face of the subject. Further, when bringing the right cheek M1 into contact with the spherical first contact member 51 and the left cheek M2 into contact with the spherical second contact member 52, the subject can freely move the spherical first and second contact members 51 and 52 to the positions that the subject find comfortable. The first contact member 51 and the second contact member 52 move when pushed by the cheeks of the subject.

As shown in FIGS. 1 and 2, the head fixing device 20 of the present embodiment is used in the binocular objective/subjective examination apparatus 1 which is an example of an ophthalmologic apparatus. When the examiner executes an eye exam away from the subject by using an ophthalmologic apparatus in which the subject needs to respond orally, it is often difficult to obtain information on the condition of the subject. For example, the examiner and the subject have more opportunities to perform exams away from each other in which the examiner performs an eye exam remotely using an information network such as the internet, to maintain social distancing.

By using the head fixing device 20, the subject can be free without having the chin and mouth of the subject restrained. As a result, the examiner can ask the subject questions and have the subject answer orally. The head fixing device 20 of the present embodiment is capable of fixing the eyes of the subject with respect to the ophthalmologic apparatus while enabling conversations required in remote examinations (examinations operated remotely) that are expected to take place in the future; thus, the head fixing device 20 can be applied to a variety of ophthalmologic apparatuses that are normally used.

In contrast, when using only the chin rest in the conventional ophthalmologic apparatuses, the position of the face of the subject, that is, the positions of the eyes of the subject, cannot always be supported stably because, depending on the shape of the face of the subject, the chin of the subject needs to be supported at one point. No matter how the subject situates his/her chin, such as clenching his/her teeth, having his/her mouth half-opened, or having his/her mouth wide open, the position of the face of the subject does not always become stable. In addition, since the chin is restrained by the chin rest, it is difficult for the subject to respond orally.

Further, when using only the forehead pad in the conventional ophthalmologic apparatuses, the head of the subject may be supported at one point, depending on the shape of the face of the subject. In such a case, the position of the face of the subject, that is, the positions of the eyes of the subject, do not always become stable.

Figure 9:
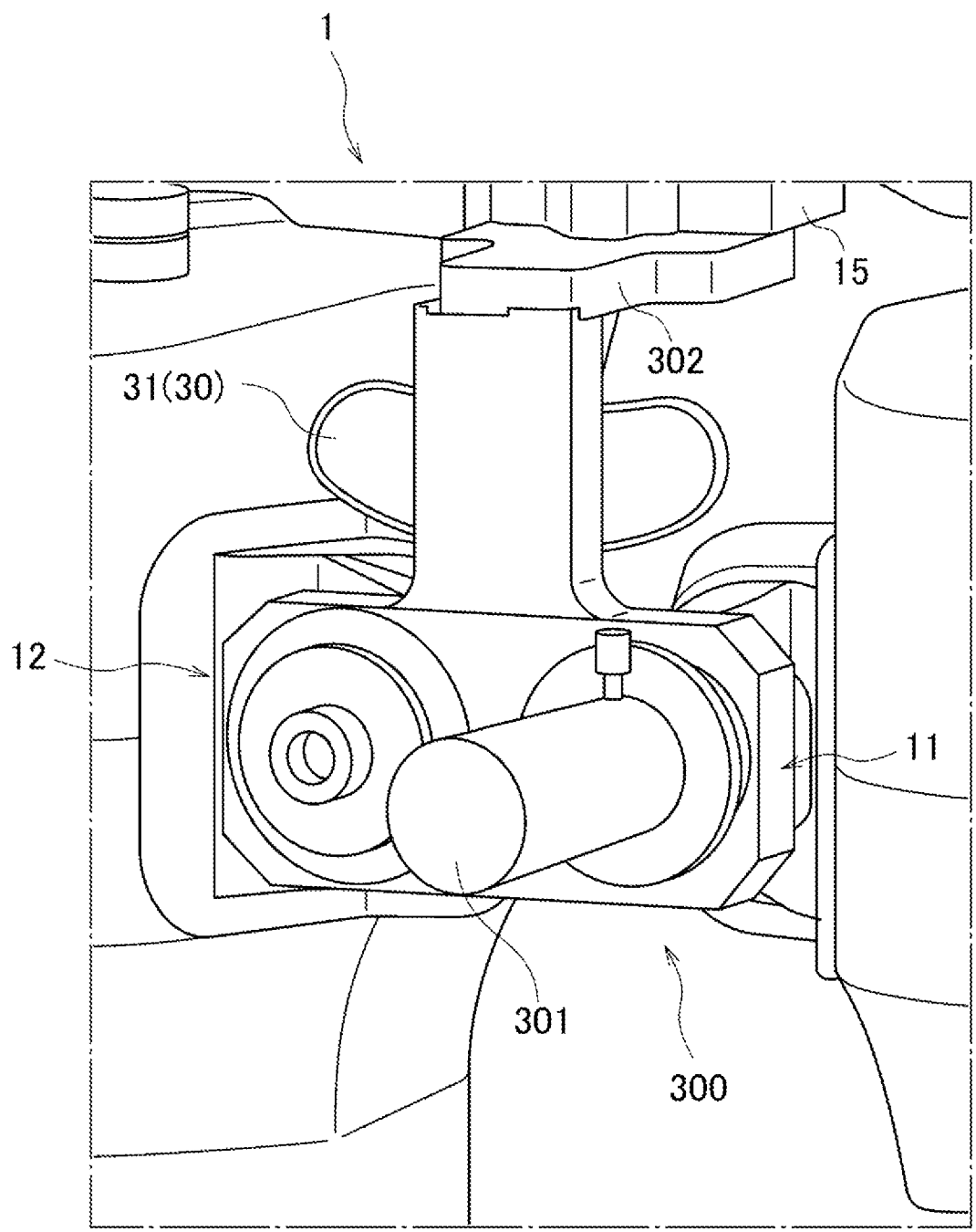
FIG. 9 is a perspective view showing an example in which a schematic eye holder is mounted in place of the head fixing device shown in FIG. 3.

FIG. 9 is a perspective view showing an example in which a schematic eye holder is mounted in place of the head fixing device shown in FIG. 3.

A schematic eye holder 300 is mounted prior to production and shipping of the binocular objective/subjective examination apparatus 1. The schematic eye holder 300 is a calibration prototype (correction prototype) for optically calibrating (correcting) the binocular objective/subjective examination apparatus 1. By mounting a schematic eye 301 such as a lens for myopia, hyperopia or the like, a correction can be executed on the optical system on the basis of the schematic eye 301, and writing of examination software of the binocular objective/subjective examination apparatus 1 can be performed.

In FIG. 9, the schematic eye holder 300 is attached to the base connecting portion 15 using an attachment plate 302 by means of, for example, screwing or the like. Thus, the schematic eye holder 300 functions as a device for attaching the schematic eye 301 to the binocular objective/subjective examination apparatus 1. The schematic eye holder 300 can perform an optical calibration (correction) of the binocular objective/subjective examination apparatus 1 by using the schematic eye 301. Thereafter, when the binocular objective/subjective examination apparatus 1 is actually shipped, the schematic eye holder 300 is removed, and an upper end portion of the support member 55 of the head fixing device 20 shown in FIG. 3 is attached to the base connecting portion 15. Since the schematic eye 301 for calibrating (correcting) the ophthalmologic apparatus is attached to the binocular objective/subjective examination apparatus 1 in this manner, the schematic eye holder 300 can be attached.

Second Embodiment

An ophthalmologic apparatus according to a second embodiment of the present invention is described next with reference to FIG. 10.

Figure 10:
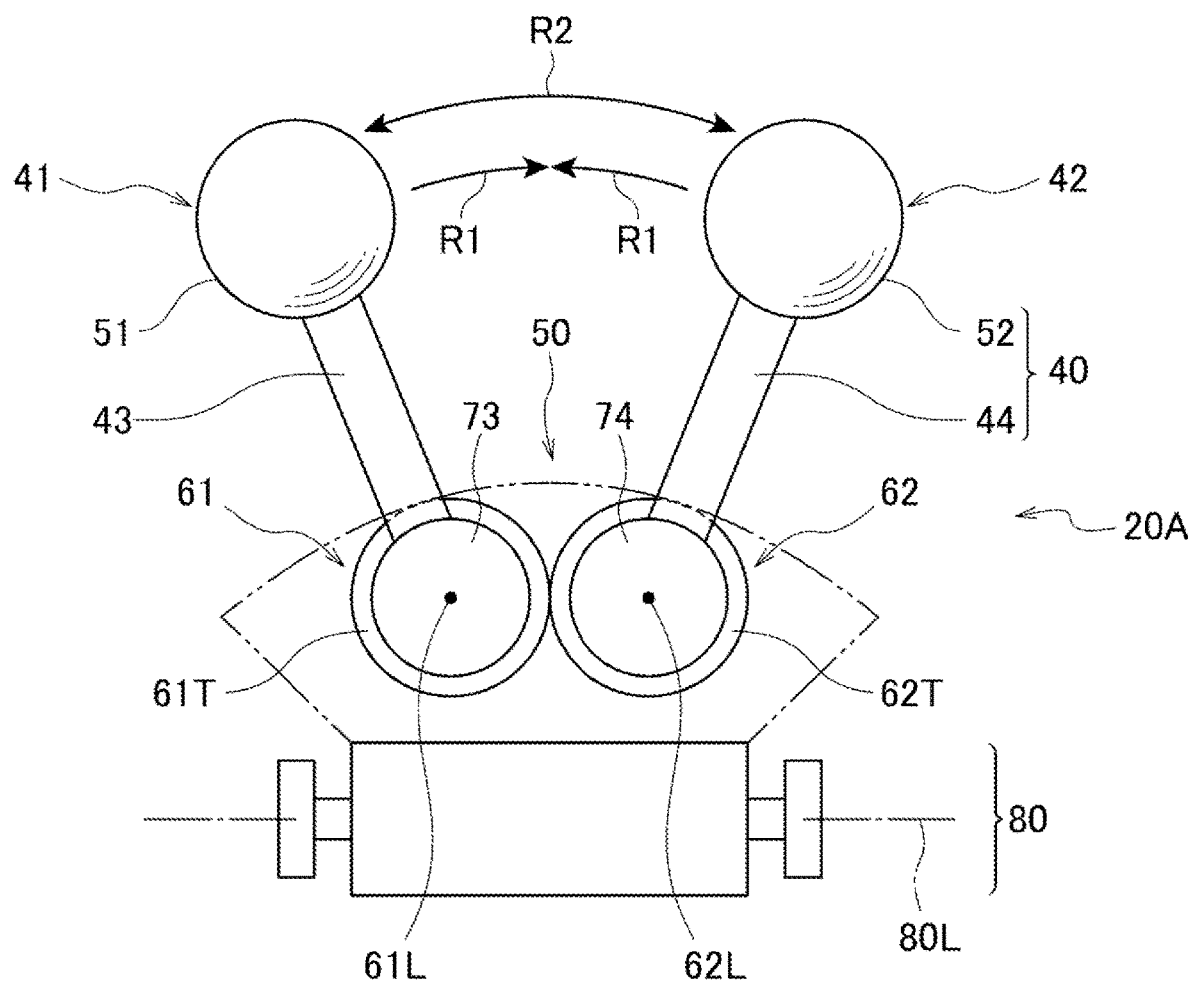
FIG. 10 is a plan view showing a head fixing device of an ophthalmologic apparatus according to a second embodiment of the present invention.

FIG. 10 is a plan view showing a head fixing device of the ophthalmologic apparatus according to the second embodiment of the present invention.

In the head fixing device 20 of the first embodiment shown in FIG. 5, the gear 71 of the first rotating body 61 and the gear 72 of the second rotating body 62 mesh with each other. In a head fixing device 20A of the second embodiment shown in FIG. on the other hand, the first rotating body 61 and the second rotating body 62 do not have gears but have ring-shaped friction materials 61T, 62T, respectively. The friction material 61T of the first rotating body 61 and the friction material 62T of the second rotating body 62 are brought into abutment against each other by a predetermined force. The first rotating body 61 and the second rotating body 62 rotate in opposite directions. Thus, in the head fixing device 20A shown in FIG. 10, the first cheek-contact body 41 and the second cheek-contact body 42 are supported so as to be openable and closable evenly to the left and right in synchronization in the directions R1 of coming close to each other and the direction R2 of separating from each other.

Third Embodiment

An ophthalmologic apparatus according to a third embodiment of the present invention is described next with reference to FIG. 11.

Figure 11:
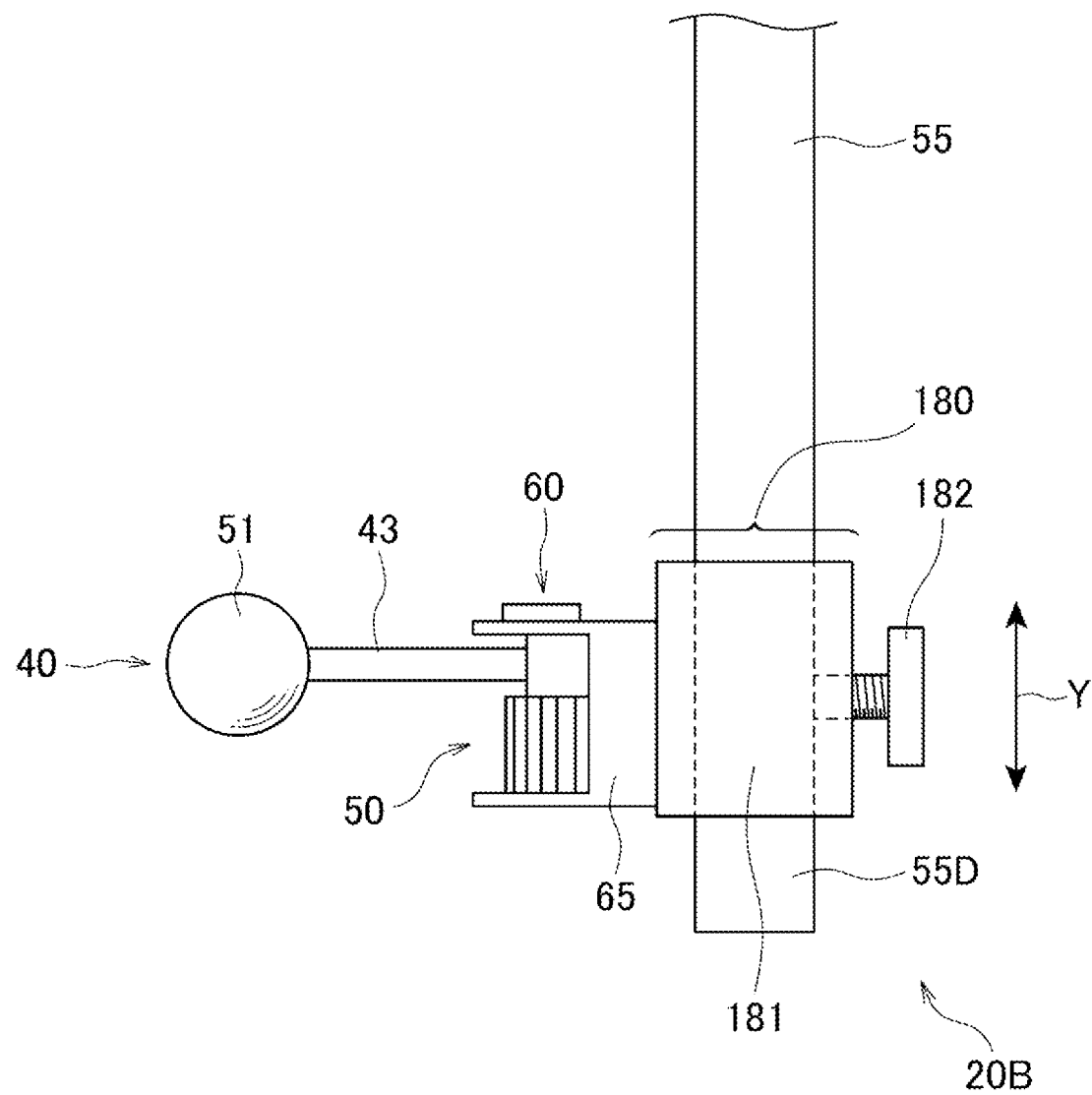
FIG. 11 is a side view showing a head fixing device of an ophthalmologic apparatus according to a third embodiment of the present invention.

FIG. 11 is a side view showing a head fixing device of the ophthalmologic apparatus according to the third embodiment of the present invention. In the head fixing device 20 according to the first embodiment shown in FIGS. 4 and 5, the opening/closing mechanism portion 50 of the cheek contact portion 40 further includes the up-down direction rotation mechanism 80 in addition to the horizontal even opening/closing mechanism 60. In a head fixing device 20B of the third embodiment shown in FIG. 11, on the other hand, the opening/closing mechanism portion 50 of the cheek contact portion 40 further includes an up-down direction movement mechanism 180 in addition to the horizontal even opening/closing mechanism 60. The up-down direction movement mechanism 180 has a cylindrical moving body 181, and a retaining screw 182 for fixing the moving body 181 at an arbitrary height position in the lower end portion 55D of the support member 55. The moving body 181 fixes the horizontal even opening/closing mechanism 60.

The support member 55 passes through the cylindrical moving body 181. The examiner can manually move the horizontal even opening/closing mechanism 60 linearly along the Y direction by loosening the retaining screw 182, and can fix the horizontal even opening/closing mechanism 60 at an arbitrary height position by tightening the retaining screw 182. Therefore, even with such a simpler mechanism as the up-down direction movement mechanism 180, the right cheek and the left cheek of the subject can be supported stably at the same height position by the spherical first and second contact members 51 and 52.

OTHER EMBODIMENTS

Figure 12A:
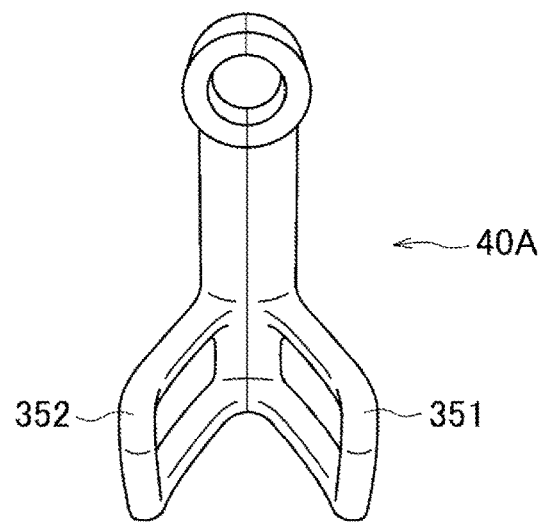
FIGS. 12A to 12C are schematic diagrams showing a cheek contact portion of an ophthalmologic apparatus according to another embodiment of the present invention.
Figure 12B:
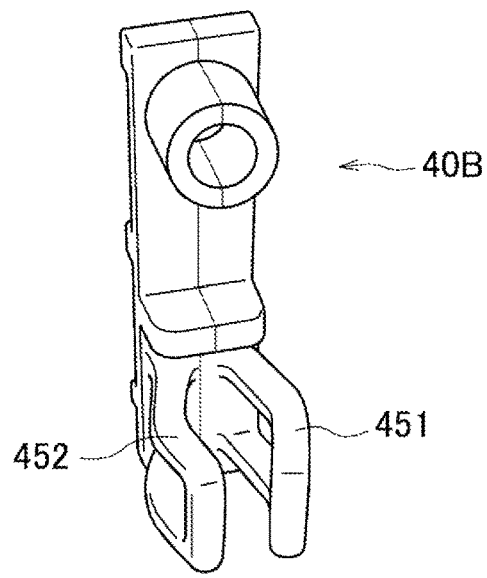
Figure 12C:
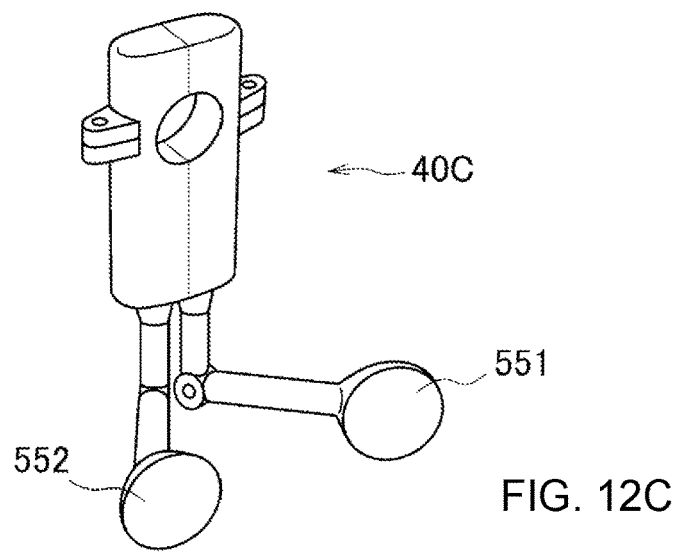

FIGS. 12A to 12C are schematic diagrams showing a cheek contact portion of an ophthalmologic apparatus according to another embodiment of the present invention.

In the ophthalmologic apparatus according to the first embodiment of the present invention shown in FIGS. 3 to 5, the first contact member 51 of the first cheek-contact body 41 of the cheek contact portion 40 and the second contact member 52 of the second cheek-contact body 42 are each a spherical object. In a cheek contact portion 40A of the embodiment shown in FIG. 12A, on the other hand, a first contact member 351 and a second contact member 352 are not spherical but are substantially U-shaped. Also, in a cheek contact portion 40B of the embodiment shown in FIG. 12B, a first contact member 451 and a second contact member 452 are formed by bending the first contact member 351 and the second contact member 352 of the embodiment shown in FIG. 12A in a direction of facing each other. In a cheek contact portion 40C according to the embodiment shown in FIG. 12C, a first contact member 551 and a second contact member 552 are not spherical but are disc-shaped. In addition to a spherical shape, the first contact member 51 and the second contact member 52 shown in FIG. 3 may be in other shapes such as a football shape and a hemispherical shape.

The embodiments of the present invention have been described above. However, the present invention is not limited to the foregoing embodiments, and therefore various modifications can be made without departing from the scope of claims. The configurations of the foregoing embodiments can be partially omitted or arbitrarily combined so as to be different from the foregoing embodiments.

Examples of the ophthalmologic apparatus according to the present invention include ophthalmologic diagnostic apparatuses, examination apparatuses, and therapeutic apparatuses. Examples of the ophthalmologic diagnostic apparatuses include three-dimensional fundus photographing apparatuses, fundus cameras, slit lamps, and optical ocular axial length measuring apparatuses. Examples of the examination apparatuses include autokerato-refractometers, autorefractometers, ophthalmotonometers, specular microscopes, autokerato-refracto tonometers, and wavefront analyzers. Examples of the therapeutic apparatuses include pattern scan lasers, laser photocoagulators, and operating microscopes.

In addition, the chin rest unit that is commonly used has an up-down drive unit for moving the chin rest up and down. The up-down drive unit may be used to drive the head fixing device of the present embodiment as described hereinafter. Specifically, the chin rest itself is removed, and the up-down drive unit is used in the head fixing device of the ophthalmologic apparatus according to the present invention. Then, the first cheek-contact body and the second cheek-contact body are opened and closed by the opening/closing mechanism portion of the cheek contact portion. The first cheek-contact body and the second cheek-contact body may or may not be moved up and down in the Y direction using the up-down drive unit. In this manner, the same effects as those of the ophthalmologic apparatus according to the present invention described above can be achieved.

Furthermore, the forehead contact portion 30 does not have to be fixed to the ophthalmologic apparatus as in the illustrated embodiments of the present invention. For example, the forehead contact portion 30 may be fixed to the support member 55 of the head fixing device 20.

What is claimed is:

1. An ophthalmologic apparatus for examining an eye of a subject, the apparatus comprising:
  a forehead contact portion coming into contact with a forehead of the subject; and
  a cheek contact portion coming into contact with cheeks of the subject, wherein
  the cheek contact portion has:
  a first cheek-contact body that supports one of the cheeks of the subject;
  a second cheek-contact body that supports the other one of the cheeks of the subject; and
  a geared opening/closing portion that opens and closes in a horizontal direction, the first cheek-contact body and the second cheek-contact body in a direction of coming close to each other and a direction of separating from each other, wherein
  the first cheek-contact body has a first shaft portion and a first contact member, the first contact member being fixed to a tip of the first shaft portion and coming into contact with the one of the cheeks,
  the second cheek-contact body has a second shaft portion and a second contact member, the second contact member being fixed to a tip of the second shaft portion and coming into contact with the other one of the cheeks,
  the geared opening/closing portion has a horizontal even opening/closing mechanism which can open and close the first cheek-contact body and the second cheek-contact body at an angle equal on left and right sides in the horizontal direction with respect to an axis in a vertical direction as a center, and
  the horizontal even opening/closing mechanism has a first rotating body and a second rotating body, the first rotating body being supported so as to be rotatable about the axis in the vertical direction as the center and having the first shaft portion fixed along a diametrical direction, the second rotating body meshing with the first rotating body, being supported so as to be rotatable about the axis in the vertical direction as the center and having the second shaft Portion fixed along the diametrical direction.

2. The ophthalmologic apparatus according to claim 1, wherein the first contact member has a spherical shape, and the second contact member has a spherical shape.

3. The ophthalmologic apparatus according to claim 1, wherein the opening/closing portion can move the first cheek-contact body and the second cheek-contact body so that the first cheek-contact body and the second cheek-contact body are at a same height position with respect to each other in a vertical direction.

4. The ophthalmologic apparatus according to claim 3, wherein the opening/closing portion can move the first cheek-contact body and the second cheek-contact body by rotating the first cheek-contact body and the second cheek-contact body in a vertical direction about an axis extending in the horizontal direction as a center, so that the first cheek-contact body and the second cheek-contact body are at a same height position with respect to each other.

5. The ophthalmologic apparatus according to claim 1, which is a subjective examination apparatus.

6. The ophthalmologic apparatus according to claim 5, wherein the subjective examination apparatus is attached to a pedestal in a state of being suspended.

7. The ophthalmologic apparatus according to claim 5, wherein the subjective examination apparatus is an objective/subjective examination apparatus for performing subjective refraction optometry and objective refraction optometry.

8. The ophthalmologic apparatus according to claim 1, wherein the cheek contact portion is attached to a base portion by a support member in a detachable manner.

9. The ophthalmologic apparatus according to claim 1, wherein a base portion is configured to attach to one of the cheek-contact portions by a support member or a schematic eye holder for mounting a schematic eye for calibration.

10. The ophthalmologic apparatus according to claim 1, wherein
- the first rotating body has a first gear and a first circular attachment portion, the first circular attachment portion being fixed above the first gear and having the first shaft portion fixed along the diametrical direction, and
- the second rotating body has a second gear and a second circular attachment portion, the second gear meshing with the first gear, the second circular attachment portion being fixed above the second gear and having the second shaft portion fixed along the diametrical direction.

* * * * *